United States Patent [19]

Wallroth et al.

[11] Patent Number: 4,579,115
[45] Date of Patent: Apr. 1, 1986

[54] DEVICE FOR SUPPLYING BREATHING GAS INTO A CLOSED VENTILATING CIRCUIT OF A MEDICAL RESPIRATOR

[75] Inventors: Carl F. Wallroth, Lubeck; Horst Frankenberger, Bad Schwartau; Anton Obermayer, Erlangen; Michael Waschmann, Lubeck; Jorg Bayerlein, Stockelsdorf, all of Fed. Rep. of Germany

[73] Assignee: Drägerwerk AG, Fed. Rep. of Germany

[21] Appl. No.: 691,448

[22] Filed: Jan. 14, 1985

[30] Foreign Application Priority Data

Jan. 17, 1983 [DE] Fed. Rep. of Germany ....... 3401384

[51] Int. Cl.[4] ............................................ A61M 16/00
[52] U.S. Cl. ........................... 128/204.21; 128/205.23
[58] Field of Search ...................... 128/204.21, 204.22, 128/204.23, 205.23

[56] References Cited

U.S. PATENT DOCUMENTS

| 3,741,208 | 6/1973 | Jonsson et al. | 128/204.21 |
| 3,951,137 | 4/1976 | Conkle et al. | 128/204.22 |
| 4,150,670 | 4/1979 | Jewett et al. | 128/204.22 |
| 4,444,201 | 4/1984 | Itoh | 128/204.23 |

Primary Examiner—Henry J. Recla
Attorney, Agent, or Firm—McGlew and Tuttle

[57] ABSTRACT

With closed respiratory systems, the patient's respiratory tract is tightly connected to a closed volume to which breathing gas is supplied only in the amount taken in by the patient. To this end, the breathing gas supply must be controlled. The controlled variable is either the pressure in the ventilating circuit, or the concentration of oxygen or the anesthetic gas in the breathing gas. A dropping pressure indicates either an increased consumption or a leak. To avoid insufficient or excessive loading of the patient, it is very important to be able to distinguish consumption from a leak. The inventive device makes this distinction possible. The breathing gas amounts are adjusted in the ventilating circuit at preset different pressures and are compared with each other, and the leak portion is computed therefrom.

6 Claims, 1 Drawing Figure

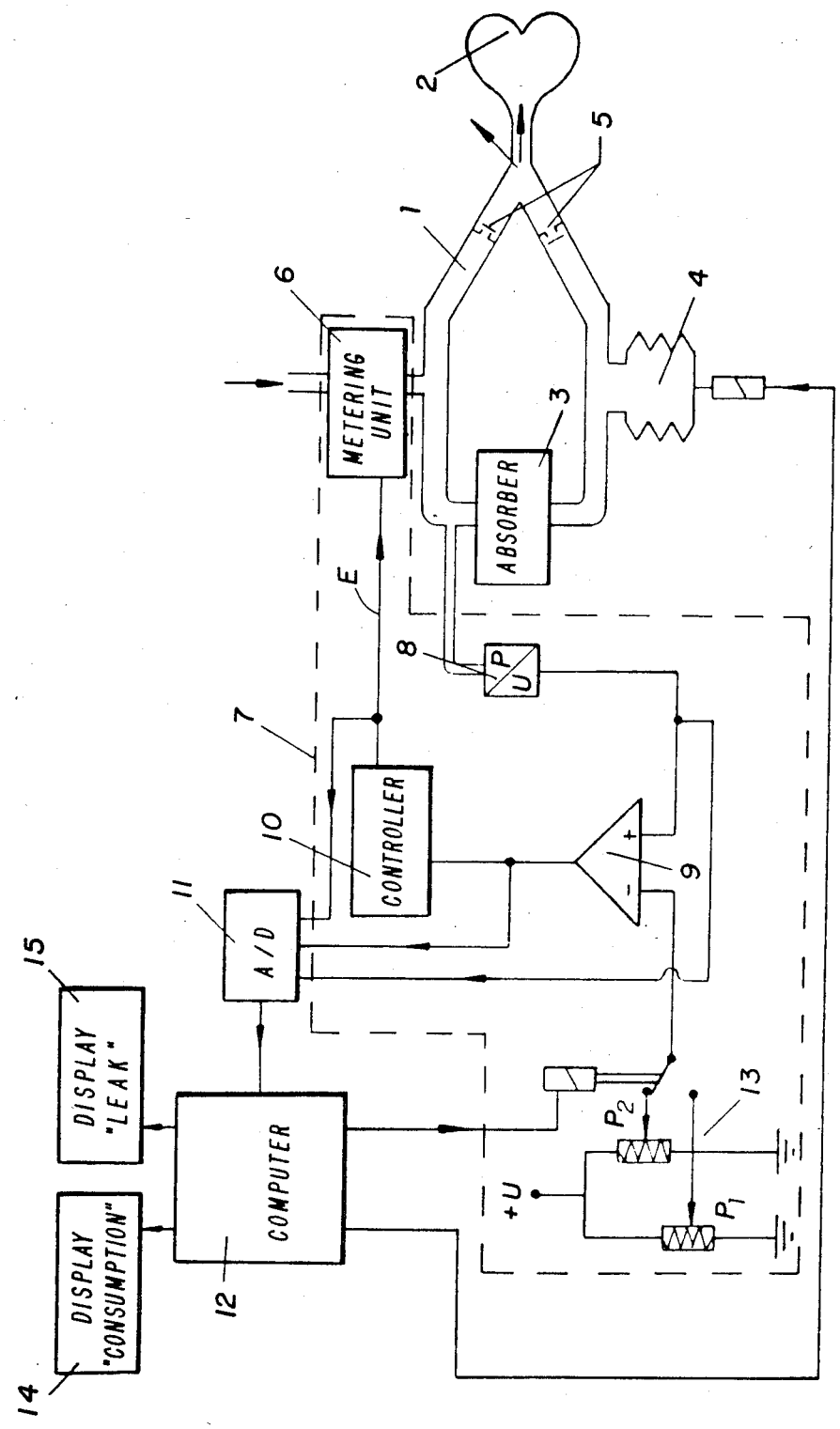

DEVICE FOR SUPPLYING BREATHING GAS INTO A CLOSED VENTILATING CIRCUIT OF A MEDICAL RESPIRATOR

FIELD AND BACKGROUND OF THE INVENTION

The present invention relates in general to respirators and in particular to a new and useful device for supplying breathing gas into a closed, volume-driven ventilating circuit of a medical respirator, which device is capable of distinguishing consumed breathing gas from leaking breathing gas.

A device of this kind is known from U.S. Pat. No. 4,127,121. This device cannot distinguish leaks from consumed gas however.

The ventilation of the patient's lungs is effected in a closed circuit. The needed oxygen and anesthetic gas are supplied through metering devices. In these devices, the consumption is determined and the difference relative to the desired value is supplied in addition. The consumption by the patient is clinically important. However, it may be determined only in a system without leaks, or where the leaking amount is known.

The U.S. Pat. No. 4,127,121 (which is incorporated here by reference) discloses a device for a monitored supply of oxygen and anesthetic gas to a patient, operating in connection with a respirator. The respirator comprises a closed ventilating circuit with a connection to the patient, a ventilation bag, a carbon dioxide absorber, and separate metering units for supplying oxygen and anesthetic gas in controlled amounts into the ventilating circuit. Each metering unit is a final element of a control circuit including a sensor, setting means, a comparator, and a controller. The oxygen control circuit measures the oxygen concentration by means of an oxygen sensor provided in the ventilating circuit, and maintains the desired value by adjusting the oxygen supply. The anesthetic gas control circuit measures, by means of a displacement sensor provided on the ventilation bag, the movement of the top of the bag, and maintains the desired value of the anesthetic gas proportion by adjusting the supply. The gas supply values of the control circuits are indicated and evaluated as consumption by the patient.

If a leak occurs in the ventilating circuit, the indicated values are a sum of the consumption by the patient plus the leak. No breakdown of the two values is possible and no leakage warning is given.

SUMMARY OF THE INVENTION

The present invention is directed to an improvement in a device of the above-mentioned kind which permits the reliable determination of the leakage proportion from the gas consumption, while utilizing the necessary gas metering.

Accordingly, an object of the present invention is to provide a device for supplying breathing gas into a closed, volume-driven ventilating circuit of a medical respirator, which comprises a metering device which is controlled by a controller which supplies an error signal to the metering device for adjusting the amount of breathing gas, or a component of the breathing gas, to be supplied to the closed circuit. A pressure is connected to the closed circuit for generating a pressure signal which is supplied to one input of a difference amplifier. The other input of the difference amplifier receives a signal corresponding to one or the other of two different preset pressure values. A volume driver is connected to the closed ventilating circuit for driving the breathing gas to the patient and a switch is provided for switching between the two preselected pressure values. An error signal is output from the difference amplifier which corresponds to the difference between the selected pressure and the actual pressure for each of the two different preselected pressure values. The output of the amplifier as well as the actual pressure value and a control output of the controller are provided, preferably through an analog-to-digital converter, to a computer which has output ports connected to the switch and the volume driver. The computer is programmed to calculate the actual consumption and a leakage value from the closed circuit based on two equations which relate the selected pressure values, the actual pressure values, the error signal from the amplifier and the control signal from the controller to achieve the calculation.

Both the consumption and the leakage values are displayed.

An advantage of the invention is that the supplied gas amount can reliably be broken down into the portion respired by the patient and the leaked portion. This not only helps to eliminate leaks and thus reduce the gas consumption but also may prevent overloading of the patient by an insufficient or excessive gas supply.

With the inventive device, a control circuit for the breathing gas which has already been mixed and which has the component of air, oxygen, and anesthetic, may be provided, or separate control circuits may similarly be used for the gases, such as an oxygen-anesthetic gas, or one of the individual gases.

A further object of the invention is to provide a device for determining breathing gas consumption as well as breathing gas leakage which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWING

The only FIGURE in the drawing is a block diagram showing the invention in terms of known and readily available elements.

DESCRIPTION OF THE PREFERRED EMBODIMENT

Referring to the drawing in particular, the invention therein comprises a device which can control the supply of breathing gas to a patient while determining the amount of breathing gas consumed as well as the amount of breathing gas leaking from a closed ventilating circuit for supplying breathing as to the patient.

The device shown as a block diagram is connected in the closed ventilating circuit 1 of a mechanical respirator. The ventilating circuit 1 is closed through the patient's lungs 2 and contains a $CO_2$ absorber 3. The breathing gas is blown in a manner known per se by means of a ventilation bellows serving as a volume drive 4. The direction of the ventilation is given by the position of check valves 5. The used breathing gas, the oxygen, and the anesthetic gas are adjusted by a metering unit 6 to which they are supplied proportionally.

A control circuit 7 having metering unit 6 as its final element uses the pressure in the ventilating circuit as its controlled variable. For this purpose, the control circuit is connected to ventilating circuit 1 through a pressure sensor 8 furnishing the actual value signal for pressure P, as a voltage U. The control circuit further comprises a differential amplifier 9 followed by a controller 10 for controlling the metering unit 6.

The actual value of the pressure P (output of pressure sensor 8), the error signal value $P_1 - P$ or $P_2 - P$ (output of differential amplifier 9), and the metered flow signal $E_1$ or $E_2$ (output of controller 10) are converted in an analog-to-digital converter 11 into a digital signal and supplied to a computer 12. A pressure switch 13 for presetting desired pressure values $P_1$ and $P_2$ determines these values for the ventilating circuit, which are then adjusted by metering unit 6 through the control of supplied amounts E to the closed circuit 1.

Computer 12 delivers signals for switching as soon as the required pressures have been reached in ventilating circuit 1 and, at the same time, volume drive 4 is stopped. With the justified assumption that the consumption V by the patient is virtually independent of the pressure within the here provided pressure range, thus remains constant for the two pressures $P_1$ and $P_2$, the following equations apply, with L being the leak in ventilating circuit 1:

$$E_1 = V + L(P_1 - P)$$

$$E_2 = V + L(P_2 - P)$$

Therefrom, the leak L and the patient's consumption V can be computed.

They are indicated or displayed as "consumption" at display 14 and "leak" at display 15.

Each of the elements shown as a block are known by the skilled artisan and can be incorporated in the invention for the stated purposes. Computer 12 can easily be programmed to perform the two equations set forth above to yield the two unknowns, namely consumption V and leak L. Since the input values from analog-to-digital converter 11 include the control signals $E_1$ and $E_2$ (from the line connecting controller 10 to metering unit 6), the actual pressure P from the pressure sensor 8 as well as the two preselected pressure $P_1$ and $P_2$ from the switching unit 13, the calculations can be performed in a simple manner. It is noted that the switching arrangement 13 includes potentiometers which can set the predetermined pressure $P_1$ and $P_2$ which are applied to a tap of the potentiometers connected between a ground and a known voltage level pulse U. It is noted that the two different preselected pressures $P_1$ and $P_2$ are at different known values, both of which are acceptable for the closed circuit. By using these two different pressure levels the two equations are obtained and these two equations can be used to calculate the two unknowns (V and L).

While a specific embodiment of the invention has been shown and described in detail to illustrate the application of the principles of the invention, it will be understood that the invention may be embodied otherwise without departing from such principles.

What is claimed is:

1. A device for supplying gas for breathing to a closed ventilating circuit having a volume driver for circulating gas in the closed circuit, comprising:

a metering unit controllable to supply a gas for breathing to the closed circuit;

a controller connected to said metering unit for applying a supply amount signal to said metering unit to control the supply of gas to the closed circuit;

a pressure sensor adapted for connection to the closed circuit for generating an actual pressure signal corresponding to an actual pressure in the closed circuit;

pressure switch means switchable to supply at least two different present pressure values for gas in the closed circuit;

a differential amplifier having a first input connected to said pressure sensor for receiving the actual pressure signal and a second input connected to said pressure switch means for receiving one of said different preset pressure values, said difference amplifier having an output connected to said controller for applying an error signal value to said controller corresponding to a difference between said actual pressure value and said one of said preset pressure values; and a computer connected to said controller for receiving said supply amount signal, to said differential amplifier output for receiving said error signal value and to said pressure sensor for receiving said actual pressure signal, said computer connected to said pressure switch means for switching between said at least two different preset pressure values and adapted for connection to the volume driver for stopping and starting operation of the volume driver, said computer including means for calculating gas consumption for a patient connected to the closed circuit and for calculating a leakage value representing leakage from the closed circuit as a function of said error signal value and said supply amount signal wherein said computer is programmed to execute the equations $$E_1 = V + L(P_1 - P)$$

$$E_2 = V + L(P_2 - P)$$

wherein, $P_1$ and $P_2$ are the at least two different present pressure valves, P is the valve of the actual pressure signal, $E_1$ and $E_2$ are valves of supply amount signals for the at least two preset pressure valves, V is the consumption amount and L is the leakage amount.

2. A device according to claim 1, including an analog-to-digital converter having one input connected to said controller, a second input connected to said differential amplifier output and a third input connected to said pressure sensor, said analog-to-digital converter having an output connected to said computer and functioning to convert said supply output signals said pressure signals and said error signal values into digital form.

3. A device according to claim 1, including a consumption display connected to said computer for displaying the consumption amount and a leakage display connected to said computer for displaying the leakage amount.

4. A device according to claim 1, wherein said metering unit is adapted to supply oxygen.

5. A device according to claim 1, wherein said metering unit adapted to supply anesthetic gas.

6. A method of operating a closed ventilating circuit having a volume driver for circulating gas in the closed circuit, comprising:

measuring the actual pressure of gas in the closed circuit to form an actual pressure signal;

obtaining a first error signal which is equal to a difference between the actual pressure signal and a first preset pressure signal;

obtaining a second pressure signal corresponding to the difference between the actual pressure signal and a second preset pressure signal;

using each of the first and second error signals to generate a first and second supply amount signal respectively for controlling an amount of gas for breathing to be supplied to the closed circuit;

using the error signals and control signals in two equations for calculating values for actual consumption of gas from the closed circuit and a leakage amount of gas from the closed circuit, the equations being $$E_1 = V + L(P_1 - P)$$

$$E_2 = V + L(P_2 - P)$$

wherein, $P_1$ and $P_2$ are the at least two different preset pressure values, P is the value of the actual pressure signal, $E_1$ and $E_2$ are values of supply amount signals for the at least two preset pressure values, V is the consumption amount and L is the leakage amount; and displaying the consumption and leakage amounts.

* * * * *